United States Patent [19]

Ecke

[11] Patent Number: 4,657,551
[45] Date of Patent: Apr. 14, 1987

[54] SHAFT FOR COLLARLESS HIP JOINT PROSTHESIS

[75] Inventor: Hermann Ecke, Giessen, Fed. Rep. of Germany

[73] Assignee: Mecron Medizinische Produkte GmbH, Berlin, Fed. Rep. of Germany

[21] Appl. No.: 497,250

[22] Filed: May 23, 1983

[30] Foreign Application Priority Data

May 21, 1982 [DE] Fed. Rep. of Germany ....... 3219681
Oct. 10, 1982 [DE] Fed. Rep. of Germany ....... 3237203

[51] Int. Cl.⁴ ............................................. A61F 2/32
[52] U.S. Cl. ..................................................... 623/23
[58] Field of Search ....................... 128/92 CA, 92 C; 3/1.91, 1.912, 1.913; 623/21, 22, 23

[56] References Cited

U.S. PATENT DOCUMENTS 3,740,769  6/1973  Haboush ............................ 3/1.912
4,080,666  3/1978  Fixel .................................. 3/1.913
4,153,953  5/1979  Grobbelaar ......................... 3/1.913

FOREIGN PATENT DOCUMENTS 0027159  4/1981  European Pat. Off. .
0038908  11/1981  European Pat. Off. .
0044915  2/1982  European Pat. Off. .
2851598  6/1980  Fed. Rep. of Germany .
1126961  9/1968  United Kingdom .

OTHER PUBLICATIONS

Richards Manufact. Co. "HJB Shoulder Prosthesis" Journal of B & J. Surg. vol. 46–A#2 Mar. 64 Adv. p. 17.

Primary Examiner—Richard J. Apley
Assistant Examiner—David J. Isabella
Attorney, Agent, or Firm—Spencer & Frank

[57] ABSTRACT

A shaft for a collarless hip joint prosthesis, the shaft having a proximal end formed to support a joint head and a distal end formed to be inserted into a bone channel, the shaft being formed to exhibit a change in the direction of its longitudinal axis in the direction of a selected plane and in a region in the vicinity of its proximal end, and having a rounded cross section presenting a reduced cross-sectional dimension in the direction perpendicular to the selected plane, the shaft having a shoulder located in the region in the vicinity of the proximal end, projecting from the selected plane, and merging in the direction of the longitudinal axis of the shaft into regions having such reduced dimension.

9 Claims, 4 Drawing Figures

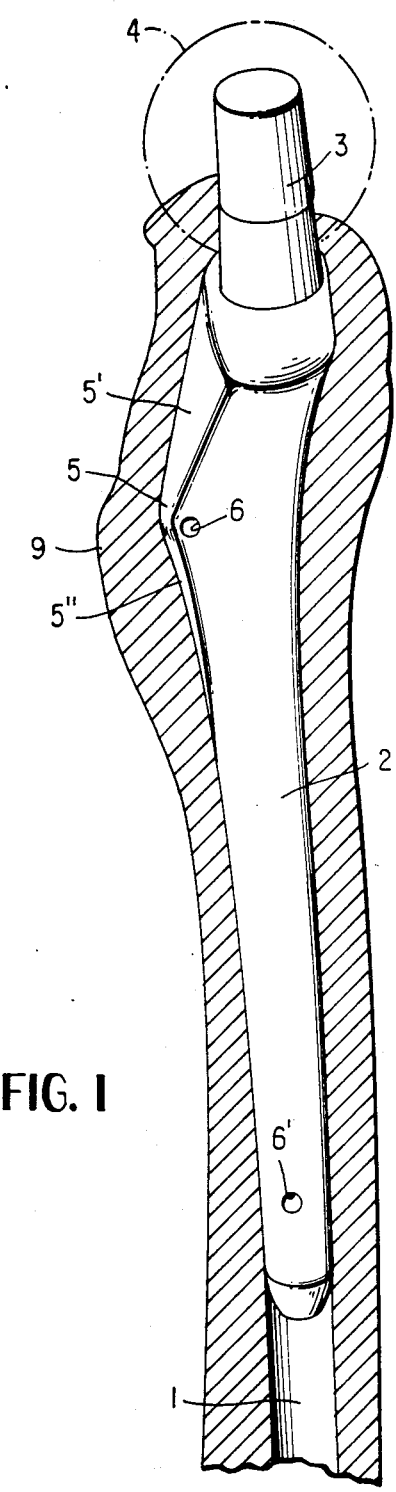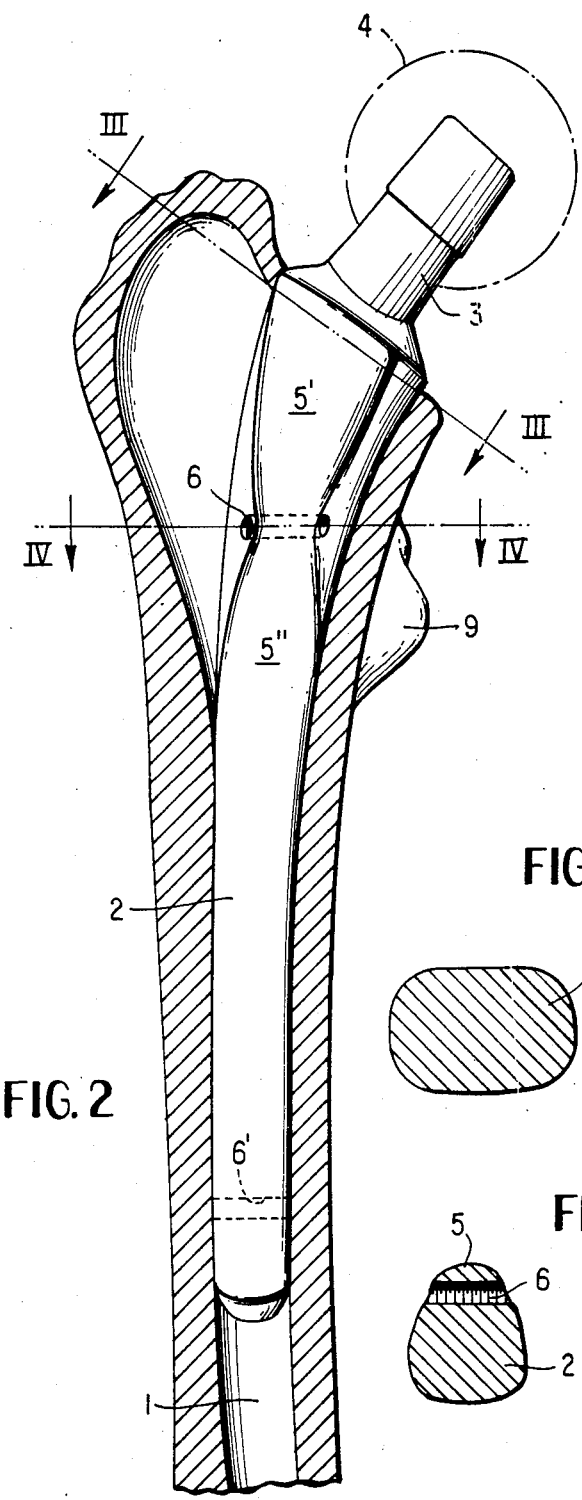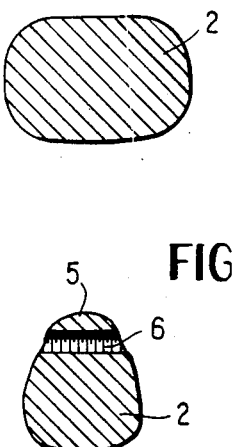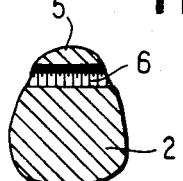

SHAFT FOR COLLARLESS HIP JOINT PROSTHESIS

BACKGROUND OF THE INVENTION

The present invention relates to a shaft for a collarless hip joint prosthesis.

Such a shaft for a collarless hip joint prosthesis can be inserted into the femur and there anchored without the use of cement.

Since certain drawbacks arise in connection with the use of bone cement, such as, for example the connection coming loose, efforts have been made to fasten endoprostheses without the use of bone cement, if possible. However, this also involves a number of difficulties. For example, if the portion of the femur which serves to receive the joint head as "collar", the introduction of force into the bone takes place only in the region of the projecting "collar" portion. But since, under such conditions, the forces exerted under load are relatively great in a narrowly defined region, the resulting "wiggling movement" may cause the prosthesis shaft to come loose.

Furthermore, collarless prostheses have become known which are tapered and wedge themselves into the drilled-out marrow chamber of the femur. Such a prosthesis is disclosed, for example, in European Pat. No. A3-0 027,159. These prostheses have the drawback that the wedge effect caused in the distal portion by the tapered prosthesis shaft is very great so that the radial stress on the bone under load is considerable and, particularly in an osteoporotic bone, there exists the danger of crack formation.

Due to the complicated configuration of the widening regions in the extreme proximal region of the shaft, it is very difficult, requiring precise measurements and normal anatomic conditions, to adapt the prosthesis to the marrow chamber in such a way that a defined force distribution results when the shaft is inserted. If the prosthesis is load bearing exclusively in this region, there again will be more or less localized stresses with the corresponding adverse results for the bone substance.

European Pat. No. A1-0 044,915 discloses a shaft portion for a collarless hip endoprosthesis which has an elliptical cross section, with the wedge fit taking place in the region of the bend or curvature of the prosthesis shaft subsequent to the Adam curve, so that, with the prosthesis under load, relatively small bending moments become effective and excessive stresses on the bone tissue are stated to be impossible. However, this prosthesis as well has the drawback that adapating the marrow chamber to the relatively complicated configuration can be accomplished only with difficulty. Moreover, the opening in the bone must be large so that the prosthesis can be inserted; this, particularly in its region having the greater curvature and the elliptical cross section, requires a larger opening than would correspond to the final cross section of the prosthesis near the joint head.

SUMMARY OF THE INVENTION

It is an object of the present invention to provide a shaft for a hip joint prosthesis of the above-mentioned type so that, on the one hand, the introduction of force is possible over an extensive area without local stresses, and on the other hand, excessive radial stresses in the region of the femur are avoided.

The above and other objects are achieved, according to the invention, by the provision of a shaft for a collarless hip joint prosthesis, the shaft having a proximal end formed to support a joint head and a distal end formed to be inserted into a bone channel, the shaft being formed to exhibit a change in the direction of its longitudinal axis in the direction of a selected plane and in a region in the vicinity of its proximal end, and having a main part with a rounded cross section which is smaller in the direction perpendicular to the selected plane than in the direction parallel to that plane, the shaft having a process, or projecting part, located in the region, projecting from the selected plane, and merging in the direction of the longitudinal axis of the shaft into such main part.

The present invention is based on the realization that the marrow channel in the region of the lesser trochanter, into which engages the process additionally provided on one side of the shaft according to the present invention, permits the introduction of forces in such a manner that a secure seat of the prosthesis is assured and the forces generated by the wedge effect are limited. At the same time the prosthesis is secured against rotation and thus loosening due to forces acting transversely to the center axis is prevented. The introduction of load forces takes place primarily in a region below the process intended for insertion into the lesser trochanter which process has a greater taper, while the task of the further distal shaft region is primarily the transmission of forces directed transversely to the longitudinal axis of the prosthesis. The reference point for the resulting moments is likewise that part of the process which is accommodated in the lesser trochanter.

The enlarged cross section in the region of the maximum curvature of the prosthesis serves preferably to accommodate a fixing bore since here a larger shaft cross section is available. In addition, a threaded fixing bore is provided in the region of the distal end. The shaft according to the present invention is preferably made of a titanium alloy or of a carbon fiber reinforced plastic.

The prosthesis shaft according to the invention thus differs basically from the prosthesis is disclosed, for example, in German Pat. No. 2,059,381 in which a bore is provided at an extension of the collar. Here, the extension is disposed on the "back" of the region of a relatively great curvature or bend. Anchoring in the lesser trochanter is impossible.

The insertion of the prosthesis is facilitated in that the cross section of the shaft in the region of the unilateral process is adapted by way of its physiological design to the cross section shortly below the end intended to receive the joint head. In this region, the rounded section is flattened on both sides, is ovoid, elliptical or oval.

With the appropriate shape of the opening in the proximal end of the bone, the prosthesis can be inserted without difficulty in that for insertion the shaft end is initially guided so as to be rotated by an angle of about 90°, until the region of the unilateral process has passed the exterior bone opening. When the region of the lesser trochanter is reached in the marrow channel, the shaft is rotated back a corresponding amount so that the shaft region having the largest cross section at the end near the joint head fits into the opening, with the shoulder being supported in the region of the lesser trochanter. This assures a secure seat for the prosthesis.

Since, if the prosthesis is configured anatomically as either a left or right prosthesis, the shaft may be relatively short, no problems occur during insertion and the movement into the suitable angular position is effected "automatically" so to speak, since further insertion is possible only in the respectively correct angular position.

According to preferred embodiments of the invention, the prosthesis is additionally provided with a slight curvature in a plane perpendicular to the plane of greater curvature, with the center point or center points of the radii of curvature being disposed on the side of the shaft opposite the unilateral process.

Other advantageous features are defined in the dependent claims. One preferred embodiment of the invention will be described in greater detail below with reference to the drawing.

BRIEF DESCRIPTION OF THE DRAWING

FIG. 1 is a side elevational view of the preferred embodiment of the prosthesis according to the present invention inserted in a left femur which is shown in cross section in the AP plane.

FIG. 2 is a rear elevational view of the same prosthesis with the femur shown in cross section in the LM plane.

FIGS. 3 and 4 are cross-sectional views of the prosthesis according to the present invention taken along two planes III—III and IV—IV, respectively, of FIG. 2.

The description below will simultaneously refer to FIGS. 1 and 2, reference being made to elements provided with the same reference numerals in both Figures. All Figures are substantially to a scale of 1:1.

DESCRIPTION OF THE PREFERRED EMBODIMENTS

The prosthesis shown in FIGS. 1 and 2 includes a shaft 2 inserted into the marrow channel of fumur 1. Shaft 2 is given a shape, in its plane of maximum curvature, which is the plane of FIG. 2 and is perpendicular to the anterior-posterior (AP) plane, such that the curvature decreases from the proximal end to the distal end. The proximal end is provided with a process, or connector, 3 which serves to accommodate a joint head 4, shown in broken lines.

The cross section of the main part of the prosthesis shaft is essentially rounded over its entire length, with the proximal end just below process 3 having the cross-sectional outline shown in FIG. 3. This outline can be called oval or ellipsoid.

This cross section decreases progressively toward the distal end while essentially maintaining—except for the unilateral process to be described below—its flattened cross-sectional shape. The smaller cross-sectional dimension is here perpendicular to the LM (lateral-medial) plane (FIG. 2), the LM plane containing the major curvature of the prosthesis shaft.

As can be seen in FIG. 1, the shaft has a further curvature of a larger radius with a center point which lies in the AP plane. The AP plane is perpendicular to the plane the larger curvature and which serves to provide adaptation to the special conditions of the left and right femurs.

The prosthesis may be made of body compatible metal alloys or of corresponding carbon fiber reinforced plastics, with the selection of material being effected in such a manner that sufficient strength is assured.

The prosthesis according to the present invention is provided with a unilateral process in the form of a shoulder 5 whose outline follows the marrow chamber in the region of the lesser trochanter 9. Shoulder 5 has an a slightly concave, essentially flat upper surface 5' which, starting from the proximal end of shaft 2, slopes downwardly away from the axis of shaft 2 to the crest of the shoulder, and a lower surface 5" which is also slightly concave and tapers from the shoulder crest downwardly until it merges with the main portion of shaft 2.

The shaft cross section shown in FIG. 4 intersects is located at the crest, or highest point, of shoulder 5, i.e. in the vicinity of a bore 6, and it can be seen that at that location the cross section of FIG. 4 is an approximation to the outline of the cross-section in the region of line III—III of FIG. 2, rotated by 90°, so that this cross-sectional region according to FIG. 4 can pass without difficulty through an opening which permits the cross-section of FIG. 3 to pass. To do this it is merely necessary to rotate the prosthesis by a given angle about the longitudinal axis, i.e. essentially the vertical axis in FIGS. 1 and 2. Since the outline of the shaft is rounded and without steps, an almost automatic guidance results during introduction into the marrow chamber.

The region of thicker material cross section in shoulder 5 serves to accommodate the bore 6, which is threaded and through which a shaft can be fixed in a selected position by means of a screw. This fixing constitutes an additional security since stable seating of the prosthesis is assured by its shape which fills the lesser trochanter.

A corresponding threaded bore 6' is also provided in the region of the distal shaft end. This bore extends in the lateral-medial direction, since this direction can easily be attained by the target device used during implantation.

It will be appreciated that without shoulder 5, shaft 2 could progressively taper toward its distal end. Then, at every point along the length of the shaft, its cross-sectional dimension in the direction of the plane of FIG. 2, which is the plane of its basic curvature, would be greater than in the direction perpendicular thereto.

The shoulder-like projection 5 according to the invention is added to this basic structure and projects from the plane of its basic curvature, i.e. extends transversely to the latter plane. The added slope imparted to the outer surface of shaft 2 by shoulder 5 is less steep in the longitudinal, or axial, direction of shaft 2 than in the circumferential direction. Thus, shoulder 5 presents an additional bulge in an otherwise essentially planar surface of shaft 2. Shoulder 5 projects laterally at a location which is essentially at the center of the inner, or concave, curvature of shaft 2 in the region of maximum curvature. In the downward direction from its crest, shoulder 5 tapers progressively for a short distance until shaft 2 again assumes its essentially oval cross section, like that of FIG. 3, which continues to taper toward the distal end.

The cross section of FIG. 4 passes essentially through the crest, or highest point, of shoulder 5. The surfaces of shoulder 5 above and below the crest have a concave curvature in a plane containing the longitudinal axis of shaft 2. The presence of shoulder 5 increases the cross section of the otherwise tapered shaft 2 on one side thereof so that the direction of the maximum cross-sec tional dimension at the location of the crest of shoulder 5 is perpendicular to the plane of basic curvature, i.e. the plane of FIG. 2.

Therefore, when shaft 2 is inserted into the opening prepared at the upper end of femur 1 for the cross section of FIG. 3, introduction of the region having the cross section of FIG. 4 can be achieved by rotating shaft 2 by 90° about its axis from the orientation it is to have in its final, seated position. Shaft 2 will then be rotated to assume its final orientation just before reaching such final position. With this last rotation, shoulder 5 comes adjacent a thickened portion of the femur structure, the trochanter minor. Thus, shoulder 5 itself acts as a pin creating a unilateral bayonet connection.

The overall dimensions of shaft 2 are thus adapted to the corresponding dimensions of the femur.

The prosthesis shown in FIGS. 1 through 4 is intended for association with the left femur. Due to the shoulder provided in the region of the lesser trochanter and due to the fact that the prosthesis is designed differently for left and right femurs and is thus asymmetrical in any case, the prosthesis can be adapted additionally to the conditions existing in the left or right femur so that an optimum seat is assured.

The region of maximum force introduction in the prosthesis according to the present invention lies in the surface region which becomes wider from the distal end to the unilateral shoulder. The resulting lip angle is dimensioned in such a way that radially directed forces are limited. The seat of the prosthesis and thus the introduction of vertical stress forces is distributed over such a large region that micromovement resulting in bone resorption is impossible. The marrow chamber opening need not be adapted in some expensive way to a complicated configuration since the prosthesis according to the present invention utilizes existing physiological conditions.

The length of the prosthesis neck may be varied during manufacture to meet individual requirements.

The screws inserted into bores 6 and 6' will extend completely through the walls of femur 1 to fix shaft 2 in place.

It will be understood that the above description of the present invention is susceptible to various modifications, changes and adaptations, and the same are intended to be comprehended within the meaning and range of equivalents of the appended claims.

What is claimed is:

1. A collarless hip prosthesis comprising a support for a joint head formed at a proximal end of a shaft, said shaft having proximal and distal regions wherein said shaft is shaped to be inserted into a femur channel and wherein said distal and proximal regions of said shaft define longitudinal axes therethrough whereby said axes intersect in said proximal region forming an obtuse angle therebetween in the direction of the lateral-medial plane of the femur; said shaft having a substantially elliptical cross section defined by a major and minor axis wherein said major axis lies in the lateral-medial plane; and said shaft further comprising, in said proximal region, a unilateral surface projection forming a shoulder, said shoulder having a slightly concave, essentially broad and flat upper end surface extending from said proximal end to a crest line located to be adjacent the lesser trochanter of the femur and in the vicinity of said intersection after said shaft has been inserted, said crest line defining a maximum cross section of said shaft and wherein the shaft defines a substantially smooth and continuous downward taper extending from said crest line to said distal end; whereby said shaft can be initially inserted into a femur channel having a generally oval opening in such a manner that the region of said unilateral projection is located so that said major axis is aligned with a major axis of the opening, and then further inserted and rotated to permit passage of the proximal region of the shaft through the opening, with the rotation serving to lock said shaft in said channel by allowing said shoulder to seat in a thickened portion of the lesser trochanter creating a unilateral bayonet connection such that minimum additional fixation is required to retain said prosthesis in the channel.

2. Shaft as defined in claim 1 wherein said main part of said shaft has an oval cross section, and said crest has a slope along the longitudinal axis of said shaft which is less than its slope transverse to that longitudinal axis.

3. Shaft as defined in claim 2 wherein said the surfaces of said surface projection on both sides of said crest are concave in the direction of the longitudinal axis of said shaft.

4. Shaft as defined in claim 1 wherein the angle has a value of substantially 90°.

5. Shaft as defined in claim 1 wherein said surface projection is provided with a through bore which is oriented essentially perpendicularly to the longitudinal axis of said shaft and extends parallel to the selected plane.

6. Shaft as defined in claim 1 provided with a bore extending transversely to the longitudinal axis of said shaft and located in the vicinity of said distal end.

7. Shaft as defined in claim 6 wherein said bore is formed to present a machine thread.

8. Shaft as defined in claim 1 wherein said shaft has a concave curvature about a center point which is disposed at the side of said shaft which is opposite said surface projection, said concave curvature having a larger radius than the curvature defining said change in direction of the longitudinal axis of said shaft.

9. Shaft as defined in claim 1 wherein the surfaces of said surface projection on both sides of said crest are concave in the direction of the longitudinal axis of said shaft.

* * * * *